US008924238B1

(12) United States Patent
Nidy et al.

(10) Patent No.: US 8,924,238 B1
(45) Date of Patent: Dec. 30, 2014

(54) METHOD AND SYSTEM FOR PROVIDING HEALTHCARE SERVICE APPOINTMENT TIME AND COST ESTIMATES AT THE TIME OF SCHEDULING

(75) Inventors: Dawn M. Nidy, Belmont, CA (US); Richard Altinger, Los Altos, CA (US); Muhammet Serdar Akin, Santa Clara, CA (US); Lisa Herrup Rogers, Palo Alto, CA (US)

(73) Assignee: Intuit Inc., Mountain View, CA (US)

( * ) Notice: Subject to any disclaimer, the term of this patent is extended or adjusted under 35 U.S.C. 154(b) by 1036 days.

(21) Appl. No.: 12/499,957

(22) Filed: Jul. 9, 2009

(51) Int. Cl.
*G06Q 50/24* (2012.01)
*G06Q 50/22* (2012.01)

(52) U.S. Cl.
CPC ............... *G06Q 50/24* (2013.01); *G06Q 50/22* (2013.01)
USPC .................................................. 705/3; 705/2

(58) Field of Classification Search
USPC ........................................ 705/2–4; 600/300
See application file for complete search history.

(56) References Cited

U.S. PATENT DOCUMENTS

| 2004/0243436 A1* | 12/2004 | Rawat et al. ...................... 705/2 |
| 2005/0234741 A1* | 10/2005 | Rana et al. ......................... 705/2 |
| 2005/0240439 A1* | 10/2005 | Covit et al. ........................ 705/2 |
| 2006/0277063 A1* | 12/2006 | Leonardi et al. .................. 705/2 |
| 2010/0106517 A1* | 4/2010 | Kociubinski et al. ............. 705/2 |

* cited by examiner

*Primary Examiner* — Michelle L Le
(74) *Attorney, Agent, or Firm* — Hawley Troxell Ennis & Hawley LLP; Philip McKay

(57) ABSTRACT

A method and system for providing healthcare service appointment time and cost estimates at the time of scheduling whereby a healthcare services database is created that includes: data indicating standardized codes associated healthcare services; data indicating the average time associated with healthcare services; data indicating the average cost of the healthcare services. One or more screening questions to be asked a patient at the time of scheduling a healthcare service appointment are then generated that indicate which, if any, of the healthcare services in the healthcare services database may be needed by the patient at the healthcare services appointment. The data in the healthcare services database is then used to schedule a healthcare service appointment for the given patient having an allocated time based on the average appointment time associated with the needed healthcare service and, in one example, the patient is provided an estimate of the cost of the healthcare service appointment based on the average cost of the needed healthcare service appointment at the time the healthcare service appointment is scheduled.

12 Claims, 4 Drawing Sheets

METHOD AND SYSTEM FOR PROVIDING HEALTHCARE SERVICE APPOINTMENT TIME AND COST ESTIMATES AT THE TIME OF SCHEDULING

BACKGROUND

The annual out-of-pocket cost to healthcare service consumers for healthcare service appointments is currently on the order of 250 billion dollars and is expected to rise to 420 billion dollars within seven years. This is due, in part, to our aging population and, in part, to many healthcare service consumers being forced to accept healthcare insurance plans with higher co-payments, higher deductibles, and lower coverage ceilings/caps. Consequently, budgeting for out-of-pocket healthcare service costs is becoming an issue for an increasing number of households and individual healthcare service consumers.

However, using current healthcare service appointment scheduling systems, a healthcare service consumer typically is given no indication of how much a healthcare service appointment is likely to cost them at the time they make the healthcare service appointment, at least beyond their minimum co-pay. Consequently, currently, when a healthcare service consumer is making a healthcare service appointment to see their doctor, or to have a follow up procedure/analysis performed, they have no idea how much to budget for the healthcare service appointment and/or follow up procedure/analysis. The result is that many healthcare service consumers are surprised by additional and/or unexpected costs associated with a healthcare service appointment and/or follow up procedure/analysis after the fact, i.e., after going to the healthcare service appointment and/or follow up procedure/analysis, and when it is too late to effectively budget for the appointment and/or follow up procedure/analysis.

In addition, healthcare service providers also suffer from the lack of ability to estimate patient costs at the time the patient is making a healthcare service appointment to see their doctor, or to have a follow up procedure/analysis performed. This is because many healthcare service providers actually collect less than 50% of the payments invoiced to healthcare service consumers for amounts not covered by healthcare insurance providers.

Making the situation even more difficult for healthcare service providers is the fact that the costs associated with generating invoices and collecting payments for healthcare related services and products are among the highest of any industry. As an example, on average, the cost of invoicing and processing healthcare payments is typically 15% or more of the dollar amount spent on the healthcare services themselves. In contrast, the cost of invoicing and processing of payments in the retail industry is typically 2% or less. The vast majority of these invoicing and processing costs in the healthcare industry are concentrated in the 250 billion dollars that healthcare service consumers pay healthcare service providers directly each year, i.e., the out-of-pocket costs the healthcare service consumers must pay beyond the portion that the healthcare insurance providers pay. However, as noted above, despite the high cost of invoicing and processing healthcare payments, many healthcare service providers actually collect less than 50% of the payments invoiced to healthcare service consumers for amounts not covered by healthcare insurance providers. As a result, the healthcare service providers not only incur the onerous invoicing and processing costs, but then, for their efforts, they still have one of the lowest actual collection rates of any industry.

To help alleviate this situation, many healthcare service providers would like to require the patient to pre-pay at least a portion of the expected patient out-of-pocket costs at the time the appointment and/or follow up procedure/analysis is scheduled. However, using current healthcare service appointment scheduling systems, and therefore without an efficient and/or reliable mechanism for estimating patient costs associated with a healthcare service appointment and/or follow up procedure/analysis at the time the healthcare service appointment and/or follow up procedure/analysis is being scheduled, healthcare service providers are typically unable to collect any portion of the expected patient out-of-pocket costs before the appointment and/or follow up procedure/analysis is performed.

In addition, for most healthcare service providers, the key to maximizing efficiency, and income, is to maximize the number of patient appointments for each business day. To this end, most healthcare service providers try to schedule an optimum number of appointments for any given business day well in advance. However, different types of patient symptoms and/or treatments require different amounts of time to address. Consequently, most healthcare service providers would benefit greatly from an ability to accurately estimate the time required for a specific patient appointment. However, using current healthcare service appointment scheduling systems, there is typically little or no accurate correlation between a patient's actual needs, as indicated by, for instance, the patient's symptoms or the patients medical history, with the amount of time allocated to the patient's appointment. As a result, healthcare service providers often either over-book their appointments, which often results in patients having to spend long periods of time in the waiting room, or under-book their appointments, resulting in blocks of "dead-time" during the work day when the healthcare service provider is incurring overhead but generating no income, i.e., when no patients are being seen and/or treated.

As noted above, in the United States, our population is aging and many healthcare service consumers are being forced to accept healthcare insurance plans with higher co-payments, higher deductibles, and lower coverage ceilings/caps. Consequently, both healthcare service consumers and healthcare service providers need more reliable mechanisms for estimating costs and making efficient use of their time. As discussed above, using currently available healthcare service appointment scheduling systems: it is difficult for healthcare service consumers to budget for healthcare service appointments early in the process, i.e., at the time the appointment is being made; it is difficult for healthcare service providers to collect advance payments for services at the time the appointment is being made; and it is difficult for healthcare service providers to efficiently and accurately allocate time for a given patient appointment based on the patient's actual needs. Consequently, currently available healthcare service appointment scheduling systems are less than ideal for both healthcare service consumers and healthcare service providers.

SUMMARY

In accordance with one embodiment, a method and system for providing healthcare service appointment time and cost estimates at the time of scheduling includes a process for providing healthcare service appointment time and cost estimates at the time of scheduling whereby, in one embodiment, a healthcare services database is created that includes: data indicating any standardized codes associated with one or more healthcare services; data indicating the average appointment time associated with the one or more healthcare services; data indicating the average cost of the one or more healthcare services. In one embodiment data representing one or more screening questions to be asked a patient at the time of scheduling a healthcare service appointment is generated. In one embodiment, the one or more screening questions to be asked a patient at the time of scheduling a healthcare service appointment are chosen such that the patient's response to the one or more questions indicates which, if any, of the one or more healthcare services in the healthcare services database may be needed by the patient at the healthcare services appointment. In one embodiment, the data in the healthcare services database is then used to determine any standardized codes associated with the needed healthcare service, the average appointment time associated with the needed healthcare service, and/or the average cost of the needed healthcare service. The patient is then scheduled for a healthcare service appointment having an allocated time based on the average appointment time associated with the needed healthcare service and/or the patient is provided an estimate of the cost of the healthcare service appointment based on the average cost of the needed healthcare service appointment, in one embodiment, at the time the healthcare service appointment is scheduled.

In one embodiment, the process for providing healthcare service appointment time and cost estimates at the time of scheduling is a stand alone system implemented on, or accessed through, a computing system. In one embodiment, the process for providing healthcare service appointment time and cost estimates at the time of scheduling is part of, accessible by, or otherwise associated with, a computing system implemented data management system. In one embodiment, the process for providing healthcare service appointment time and cost estimates at the time of scheduling is part of, accessible by, or otherwise associated with, a computing system implemented healthcare management system. In one embodiment, the process for providing healthcare service appointment time and cost estimates at the time of scheduling is part of, accessible by, or otherwise associated with, a computing system implemented healthcare service appointment scheduling system.

In one embodiment, data indicating one or more healthcare services provided by a given healthcare service provider is obtained by process for providing healthcare service appointment time and cost estimates at the time of scheduling. In one embodiment, the data indicating one or more healthcare services provided by the given healthcare service provider is obtained by asking the given healthcare service provider for the information. In one embodiment, the data indicating one or more healthcare services provided by the given healthcare service provider is obtained by analyzing the healthcare service provider's records. In one embodiment, the data indicating one or more healthcare services provided by the given healthcare service provider is obtained by analyzing a healthcare insurance provider's records. In other embodiments, data indicating one or more healthcare services provided by the given healthcare service provider is obtained by any means for obtaining data indicating one or more healthcare services provided by the given healthcare service provider discussed herein, and/or known in the art at the time of filing, and/or as developed after the time of filing.

In one embodiment, data indicating any standardized codes associated with the one or more healthcare services provided by the given healthcare service provider is obtained and correlated to the respective one or more healthcare services provided by the given healthcare service provider.

In one embodiment, the standardized codes are codes generated and/or used by professional associations, such as the American Medical Association (AMA). For instance, in one embodiment, AMA provided CPT codes indicating defined medical procedures are used and correlated to one or more healthcare services provided by the given healthcare service provider. Likewise, in one embodiment, ICD9 codes from the AMA indicating defined diagnoses are used and correlated to one or more healthcare services provided by the given healthcare service provider.

In other embodiments, other codes provided by other organizations are used, such as, but not limited to, healthcare insurance provider codes, codes used by a healthcare service provider, or codes used by a government agency. In other embodiments, any standardized codes associated with the one or more healthcare services provided by the given healthcare service provider as discussed herein, and/or as known in the art at the time of filing, and/or as developed after the time of filing, are used and are obtained from any source of these codes as discussed herein, and/or as known in the art at the time of filing, and/or as developed after the time of filing.

In one embodiment, data indicating the average appointment time associated with the one or more healthcare services provided by the given healthcare service provider is obtained and correlated to the respective one or more healthcare services provided by the given healthcare service provider. In one embodiment the average appointment time associated with the one or more healthcare services provided by the given healthcare service provider is determined based on the standardized codes associated with the one or more healthcare services provided by the given healthcare service provider. In one embodiment, the average appointment time associated with the one or more healthcare services provided by the given healthcare service provider is determined based on analysis of the healthcare service provider's records. In one embodiment, the average appointment time associated with the one or more healthcare services provided by the given healthcare service provider is determined based on analysis of a healthcare insurance provider's records. In some embodiments, the average appointment time associated with the one or more healthcare services provided by the given healthcare service provider is determined based on analysis of any data from any source of data indicating the average appointment time associated with the one or more healthcare services provided by the given healthcare service provider as discussed herein, and/or as known in the art at the time of filing, and/or as developed after the time of filing.

In one embodiment, data indicating the average cost of the one or more healthcare services provided by the given healthcare service provider is obtained and correlated to the respective one or more healthcare services provided by the given healthcare service provider. In one embodiment, the average cost of the one or more healthcare services provided by the given healthcare service provider is determined based on the standardized codes associated with the one or more healthcare services provided by the given healthcare service provider. In one embodiment, the average cost of the one or more healthcare services provided by the given healthcare service provider is determined based on analysis of the healthcare service provider's records. In one embodiment, the average cost of the one or more healthcare services provided by the given healthcare service provider is determined based on analysis of a healthcare insurance provider's records. In some embodiments, the average cost of the one or more healthcare services provided by a given healthcare service provider is determined based on analysis of any data from any source of data indicating the average cost of the one or more healthcare services provided by the given healthcare service provider as discussed herein, and/or as known in the art at the time of filing, and/or as developed after the time of filing.

In one embodiment: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in a healthcare services database.

In one embodiment, one or more screening questions to be asked a patient at the time of scheduling a healthcare service appointment are chosen and/or generated. In one embodiment, the one or more screening questions to be asked a patient at the time of scheduling a healthcare service appointment are chosen such that the patient's response to the one or more screening questions to be asked a patient at the time of scheduling a healthcare service appointment indicates which, if any, of the one or more healthcare services provided by the given healthcare service provider in the healthcare services database may be needed by the patient at the healthcare service appointment. For instance, in one embodiment, the one or more screening questions to be asked a patient at the time of scheduling a healthcare service appointment request information regarding the patient's symptoms. As another example, in one embodiment, the one or more screening questions to be asked a patient at the time of scheduling a healthcare service appointment request information regarding the patient's medical history. As another example, in one embodiment, the one or more screening questions to be asked a patient at the time of scheduling a healthcare service appointment request information regarding the patient's previous appointments with the healthcare service provider and/or if the patient has scheduled this type of healthcare service appointment before. As another example, in one embodiment, the one or more screening questions to be asked a patient at the time of scheduling a healthcare service appointment request information regarding the patient's healthcare insurance coverage. In other embodiments, the one or more screening questions to be asked a patient at the time of scheduling a healthcare service appointment request any information regarding the patient's health and/or healthcare status that the provider of the process for providing healthcare service appointment time and cost estimates at the time of scheduling and/or the healthcare service provider determines may help associate the appointment being scheduled with any of the one or more healthcare services provided by a given healthcare service provider in the healthcare services database.

In one embodiment, the data representing the one or more screening questions to be asked a patient at the time of scheduling a healthcare service appointment is stored in a screening questions database that may, or may not, be the same database as the healthcare services database.

In one embodiment, a computing system implemented healthcare service appointment scheduling system is provided and the computing system implemented healthcare service appointment scheduling system is provided access to the data in the healthcare services database and/or the screening questions database.

In one embodiment, the computing system implemented healthcare service appointment scheduling system is provided access to the process for providing healthcare service appointment time and cost estimates at the time of scheduling and/or the data in the healthcare services database and/or the screening questions database, but is independent of the process for providing healthcare service appointment time and cost estimates at the time of scheduling and/or a computing system implemented data management system.

In one embodiment, the computing system implemented healthcare service appointment scheduling system is provided access to the process for providing healthcare service appointment time and cost estimates at the time of scheduling and/or the data in the healthcare services database and/or the screening questions database via a website and/or any network, as discussed herein, and/or as known in the art at the time of filing, and/or as developed after the time of filing.

In one embodiment, the computing system implemented healthcare service appointment scheduling system is provided access to the process for providing healthcare service appointment time and cost estimates at the time of scheduling and/or the data in the healthcare services database and/or the screening questions database by providing the computing system implemented healthcare service appointment scheduling system access to a computing system, and/or a server system, under the control of one or more healthcare service providers, and/or any third party.

In one embodiment, the computing system implemented healthcare service appointment scheduling system is provided access to the process for providing healthcare service appointment time and cost estimates at the time of scheduling and/or the data in the healthcare services database and/or the screening questions database using a computer program product as defined herein.

In other embodiments, the computing system implemented healthcare service appointment scheduling system is provided access to the process for providing healthcare service appointment time and cost estimates at the time of scheduling and/or the data in the healthcare services database and/or the screening questions database using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, when the computing system implemented healthcare service appointment scheduling system is being used to schedule a given healthcare service appointment for a given patient, the given patient is asked the one or more screening questions to be asked a patient at the time of scheduling a healthcare service appointment. In one embodiment, the given patient is asked the one or more screening questions to be asked a patient at the time of scheduling a healthcare service appointment via a "wizard" such as an appointment "scheduling wizard" that requests responses to the one or more screening questions to be asked a patient at the time of scheduling a healthcare service appointment via pop-up windows and/or data entry fields. In one embodiment, the given patient is asked the one or more screening questions to be asked a patient at the time of scheduling a healthcare service appointment via an automated phone response system. In one embodiment, the given patient is asked the one or more screening questions to be asked a patient at the time of scheduling a healthcare service appointment via questions asked by an employee of, or agent for, the healthcare services provider over the phone. In one embodiment, the given patient is asked the one or more screening questions to be asked a patient at the time of scheduling a healthcare service appointment via questions asked by an employee of, or agent for, the healthcare services provider in person. In other embodiments, the given patient is asked the one or more screening questions to be asked a patient at the time of scheduling a healthcare service appointment via any means, mechanism and/or process for asking, and receiving responses to, the one or more screening questions to be asked a patient at the time of scheduling a healthcare service appointment discussed herein, and/or as known in the art at the time of filing, and/or as developed after the time of filing.

As noted above, in one embodiment, the one or more screening questions to be asked a patient at the time of scheduling a healthcare service appointment are chosen such that the patient's response to the one or more screening questions to be asked a patient at the time of scheduling a healthcare service appointment indicates which, if any, of the one or more healthcare services provided by the given healthcare service provider in the healthcare services database may be needed by the patient at the healthcare service appointment. Consequently, in one embodiment, based on the patient's responses to the one or more screening questions to be asked a patient at the time of scheduling a healthcare service appointment, at least one of the one or more healthcare services provided by the given healthcare service provider in the healthcare services database is identified as being required at the given healthcare service appointment being scheduled.

In one embodiment, once the healthcare service required at the given healthcare service appointment is identified, the data in the healthcare services database is used to determine any standardized codes associated with the healthcare service required at the given healthcare service appointment.

In one embodiment, based on the patient's responses to the one or more screening questions to be asked a patient at the time of scheduling a healthcare service appointment, and/or any standardized codes associated with the healthcare service required at the given healthcare service appointment, the data in the healthcare services database is used to determine the average amount of time required for healthcare service appointments involving the healthcare service required by the given patient at the given healthcare service appointment. In one embodiment, the given patient is then scheduled for the given healthcare service appointment and the given healthcare service appointment is allocated an amount of time based on the average amount of time required for healthcare service appointments involving the healthcare service required at the given healthcare service appointment.

In one embodiment, based on the patient's responses to the one or more screening questions to be asked a patient at the time of scheduling a healthcare service appointment, and/or any standardized codes associated with the healthcare service required at the given healthcare service appointment, the data in the healthcare services database is used to determine the average cost for the healthcare service required by the given patient at the given healthcare service appointment.

In one embodiment data regarding the patient's healthcare insurance coverage is obtained and then the average cost for the healthcare service required at the given healthcare service appointment and the data regarding the patient's healthcare insurance coverage is used to provide the given patient an estimate of the given patient's out-of-pocket costs for the given healthcare service appointment at the time the given healthcare service appointment is scheduled. In one embodiment, the patient is also provided the opportunity to pre-pay all, or part, of the estimated out-of-pocket costs for the given healthcare service appointment at the time the given healthcare service appointment is scheduled.

Using the method and system for providing healthcare service appointment time and cost estimates at the time of scheduling discussed herein, both healthcare service consumers and healthcare service providers are provided a reliable and efficient mechanism for estimating healthcare service costs and the time to be allocated to healthcare service appointments, at the time the healthcare service appointments are being scheduled. In particular, using the method and system for providing healthcare service appointment time and cost estimates at the time of scheduling discussed herein: healthcare service consumers are provided the information needed to budget for healthcare service appointments early in the process, i.e., at the time the healthcare service appointment is being made; healthcare service providers are provided the information necessary, and mechanism, to collect advance payments for healthcare services at the time the healthcare service appointment is being made; and healthcare service providers are provided the information necessary, and mechanism, to efficiently and accurately allocate time for a given patient's given healthcare service appointment based on the patient's actual needs. Consequently, the method and system for providing healthcare service appointment time and cost estimates at the time of scheduling discussed herein benefits both healthcare service consumers and healthcare service providers.

As discussed in more detail below, using the below embodiments, with little or no modification and/or user input, there is considerable flexibility, adaptability, and opportunity for customization to meet the specific needs of various users under numerous circumstances.

Figure 1:
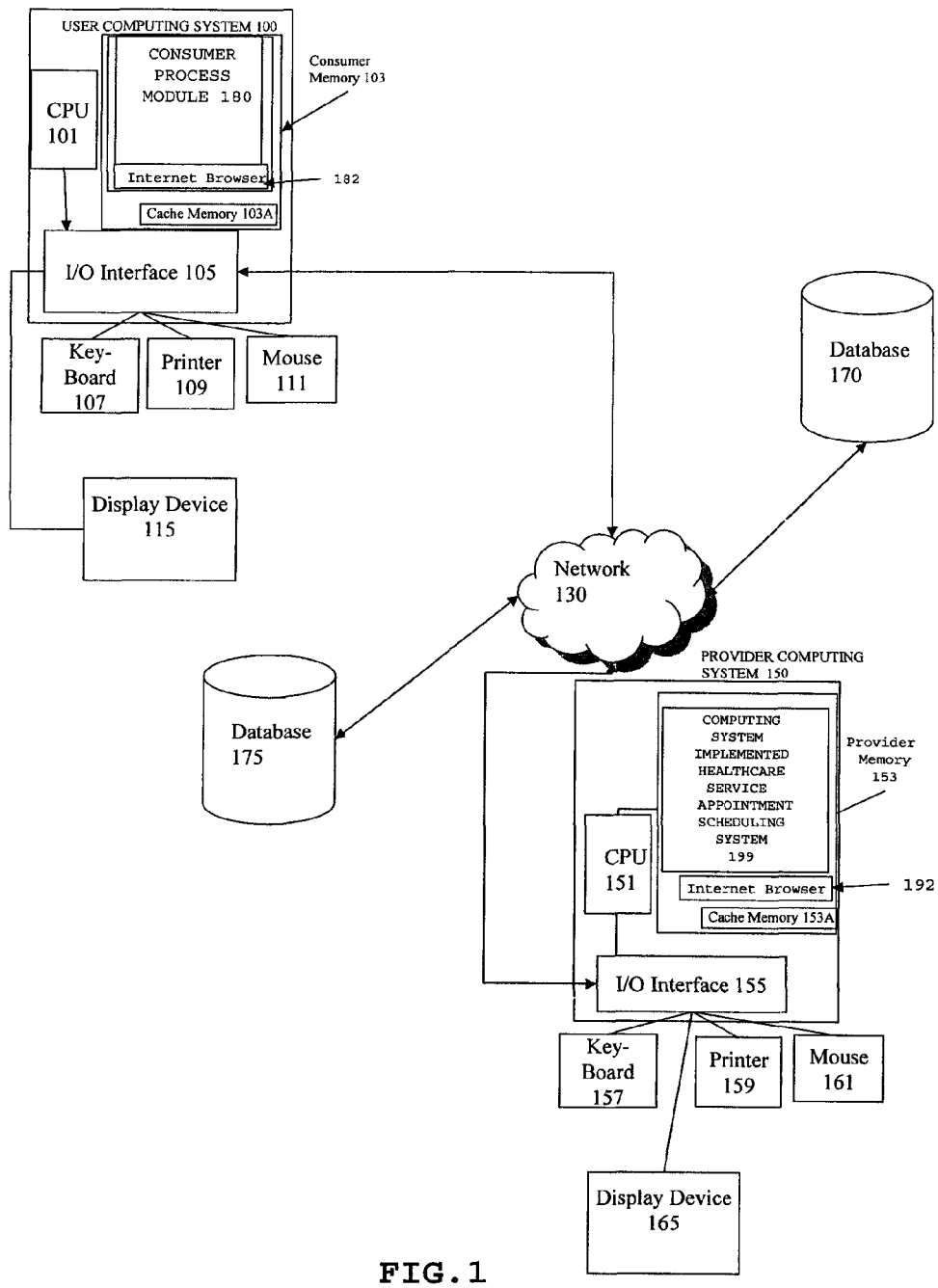
FIG. 1 is a block diagram of an exemplary hardware architecture for implementing one embodiment including a consumer computing system, a provider computing system, a database, and a network.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

In accordance with one embodiment, a method and system for providing healthcare service appointment time and cost estimates at the time of scheduling includes a process for providing healthcare service appointment time and cost estimates at the time of scheduling whereby, in one embodiment, a healthcare services database is created that includes: data indicating any standardized codes associated with one or more healthcare services; data indicating the average appointment time associated with the one or more healthcare services; data indicating the average cost of the one or more healthcare services. In one embodiment data representing one or more screening questions to be asked a patient at the time of scheduling a healthcare service appointment is generated. In one embodiment, the one or more screening questions to be asked a patient at the time of scheduling a healthcare service appointment are chosen such that the patient's response to the one or more questions indicates which, if any, of the one or more healthcare services in the healthcare services database may be needed by the patient at the healthcare services appointment. In one embodiment, the data in the healthcare services database is then used to determine any standardized codes associated with the needed healthcare service, the average appointment time associated with the needed healthcare service, and/or the average cost of the needed healthcare service. The patient is then scheduled for a healthcare service appointment having an allocated time based on the average appointment time associated with the needed healthcare service and/or the patient is provided an estimate of the cost of the healthcare service appointment based on the average cost of the needed healthcare service appointment, in one embodiment, at the time the healthcare service appointment is scheduled.

FIG. 1 is a block diagram of an exemplary hardware architecture for implementing one embodiment of a system and method for providing healthcare service appointment time and cost estimates at the time of scheduling, such as exemplary process 400 (FIG. 4) discussed herein, that, returning to FIG. 1, includes: a consumer computing system 100, e.g., a first computing system; a provider computing system 150, e.g., a second computing system; a database 170; and a database 175, all operatively coupled by a network 130.

As seen in FIG. 1, consumer computing system 100 typically includes one or more central processing units, CPU(s) 101, an input/output (I/O) interface 105, and a consumer memory 103, including cache consumer memory 103A. As discussed in more detail below, in one embodiment, consumer memory 103 includes all, or part, of instructions and data associated with a process for providing healthcare service appointment time and cost estimates at the time of scheduling 400 (see FIG. 4), and, in particular, a consumer process module 180.

Returning to FIG. 1, consumer computing system 100 may further include standard user interface devices such as a keyboard 107, a mouse 111, a printer 109, and a display device 115, as well as, one or more standard input/output (I/O) devices (not shown), such as a compact disk (CD) or Digital Video Disc (DVD) drive, floppy disk drive, or other digital or waveform port, or other device capable of inputting data to, and outputting data from, consumer computing system 100, whether available or known at the time of filing or as later developed.

In one embodiment, consumer computing system 100 also includes an Internet browser capability 182 that, in one embodiment, includes a search engine (not shown) and is stored, in whole, or in part, in consumer memory 103.

In one embodiment, consumer computing system 100 is a computing system accessible by one or more users. In one embodiment, consumer computing system 100 is used, and/or accessible, by another computing system, such as provider computing system 150 (discussed below).

In one embodiment, consumer computing system 100 is representative of multiple consumer computing systems. In one embodiment, consumer computing system 100 is representative of a webpage, or web-based system. In one embodiment, consumer computing system 100 is a server computing system. In various embodiments, consumer computing system 100 is any computing system as defined herein and/or as known in the art at the time of filing and/or as developed thereafter, that includes components that can execute all, or part, of a process for providing healthcare service appointment time and cost estimates at the time of scheduling in accordance with at least one of the embodiments as described herein.

As also seen in FIG. 1, provider computing system 150 typically includes one or more central processing units, CPU(s) 151, an input/output (I/O) interface 155, and a provider memory 153, including cache memory 153A. As discussed in more detail below, in one embodiment, provider memory 153 includes all, or part, of instructions and data associated with a computing system implemented healthcare service appointment scheduling system 199.

Returning to FIG. 1, provider computing system 150 may further include standard user interface devices such as a keyboard 157, a mouse 161, a printer 159, and a display device 165, as well as, one or more standard input/output (I/O) devices (not shown), such as a compact disk (CD) or Digital Video Disc (DVD) drive, floppy disk drive, or other digital or waveform port, or other device capable of inputting data to, and outputting data from, provider computing system 150, whether available or known at the time of filing or as later developed.

In one embodiment, provider computing system 150 also includes an Internet browser capability 192 that, in one embodiment, includes a search engine (not shown) and is stored, in whole, or in part, in provider memory 153.

In one embodiment, provider computing system 150 is used, and/or is accessible, by another computing system, such as consumer computing system 100.

In one embodiment, provider computing system 150 is representative of multiple provider computing systems. In one embodiment, provider computing system 150 is representative of a webpage, or web-based system. In one embodiment, provider computing system 150 is a server computing system. In one embodiment, provider computing system 150 is a web-server computing system. In various embodiments, provider computing system 150 is any computing system as defined herein and/or as known in the art at the time of filing and/or as developed thereafter, that includes components that can execute all, or part, of a process for providing healthcare service appointment time and cost estimates at the time of scheduling in accordance with at least one of the embodiments as described herein.

Also shown in FIG. 1 is database 170. In one embodiment, database 170 is a data storage device, a designated server system or computing system, or a designated portion of one or more server systems or computing systems, such as computing systems 100 and/or 150, or a distributed database, or an external and/or portable hard drive. In one embodiment, database 170 is a dedicated mass storage device implemented in software, hardware, or a combination of hardware and software. In one embodiment, database 170 is a healthcare services database. In one embodiment, database 170 includes a web-based function. As discussed in more detail below, in one embodiment, database 170 is under the control of, or otherwise accessible by, a process for providing healthcare service appointment time and cost estimates at the time of scheduling.

In one embodiment, data associated with a process for providing healthcare service appointment time and cost estimates at the time of scheduling, and/or data associated with one or more healthcare services, is stored, in whole, or in part, in database 170, and is used by, or is accessed by, a process for providing healthcare service appointment time and cost estimates at the time of scheduling. In one embodiment, database 170 is accessible by one or more users. In one embodiment, database 170 is used, and/or accessible, by a computing system, such as computing systems 100 and/or 150.

Also shown in FIG. 1 is database 175. In one embodiment, database 175 is a data storage device, a designated server system or computing system, or a designated portion of one or more server systems or computing systems, such as computing systems 100 and/or 150, or a distributed database, or an external and/or portable hard drive. In one embodiment, database 175 is a dedicated mass storage device implemented in software, hardware, or a combination of hardware and software. In one embodiment, database 175 is a screening questions database. In one embodiment, database 175 includes a web-based function. As discussed in more detail below, in one embodiment, database 175 is under the control of, or otherwise accessible by, a process for providing healthcare service appointment time and cost estimates at the time of scheduling.

In one embodiment, data associated with a process for providing healthcare service appointment time and cost estimates at the time of scheduling, and/or data associated with one or more healthcare services, is stored, in whole, or in part, in database 175, and is used by, or is accessed by, a process for providing healthcare service appointment time and cost estimates at the time of scheduling. In one embodiment, database 175 is accessible by one or more users. In one embodiment, database 175 is used, and/or accessible, by a computing system, such as computing systems 100 and/or 150.

In one embodiment, computing systems 100 and 150, and databases 170 and 175, are communicably coupled through network 130. Network 130 can be any network or network system as defined herein, and/or known in the art at the time of filing, and/or as developed after the time of filing, capable of allowing communication between two or more computing systems, server systems, and/or databases.

In one embodiment, computing systems 100 and 150, databases 170 and 175, and network 130 are part of a cloud computing environment.

Those of skill in the art will readily recognize that the components shown in FIG. 1, such as computing systems 100 and 150, and databases 170 and 175, and their respective components, are shown for illustrative purposes only and that architectures with more or fewer components can implement, and benefit from, one or more embodiments. Moreover, one or more components of consumer computing system 100, provider computing system 150, and databases 170 and 175, may be located remotely from their respective system and accessed via network 130. In addition, the particular type of, and configuration of, computing systems 100 and 150 are not relevant.

Figure 4:
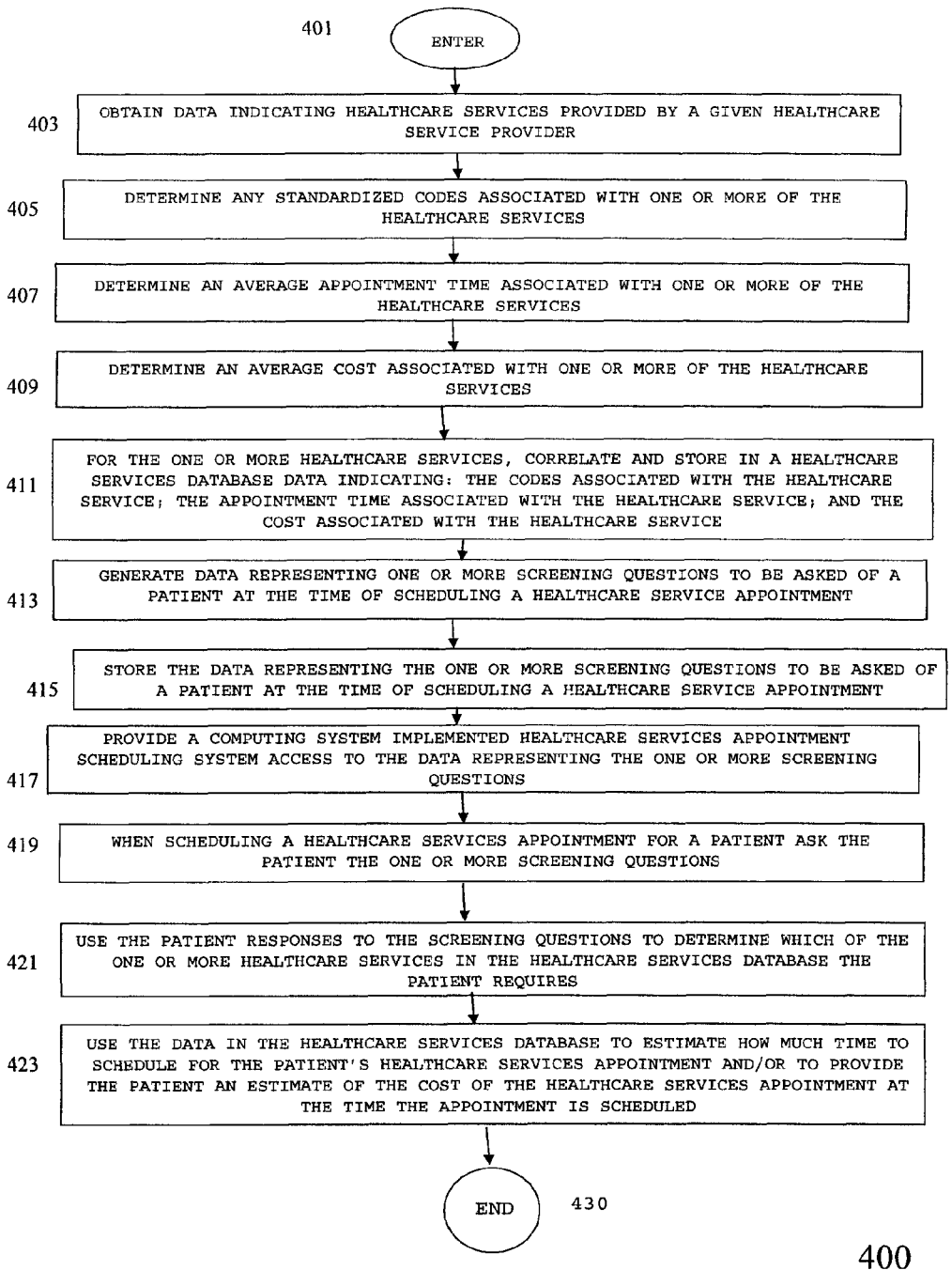
FIG. 4 is an exemplary flow chart illustrating one embodiment of a process for providing healthcare service appointment time and cost estimates at the time of scheduling.

As discussed above, in one embodiment, at least part of consumer memory 103 includes all, or part, of instructions and data associated with a process for providing healthcare service appointment time and cost estimates at the time of scheduling 400 (see FIG. 4.).

Figure 2:
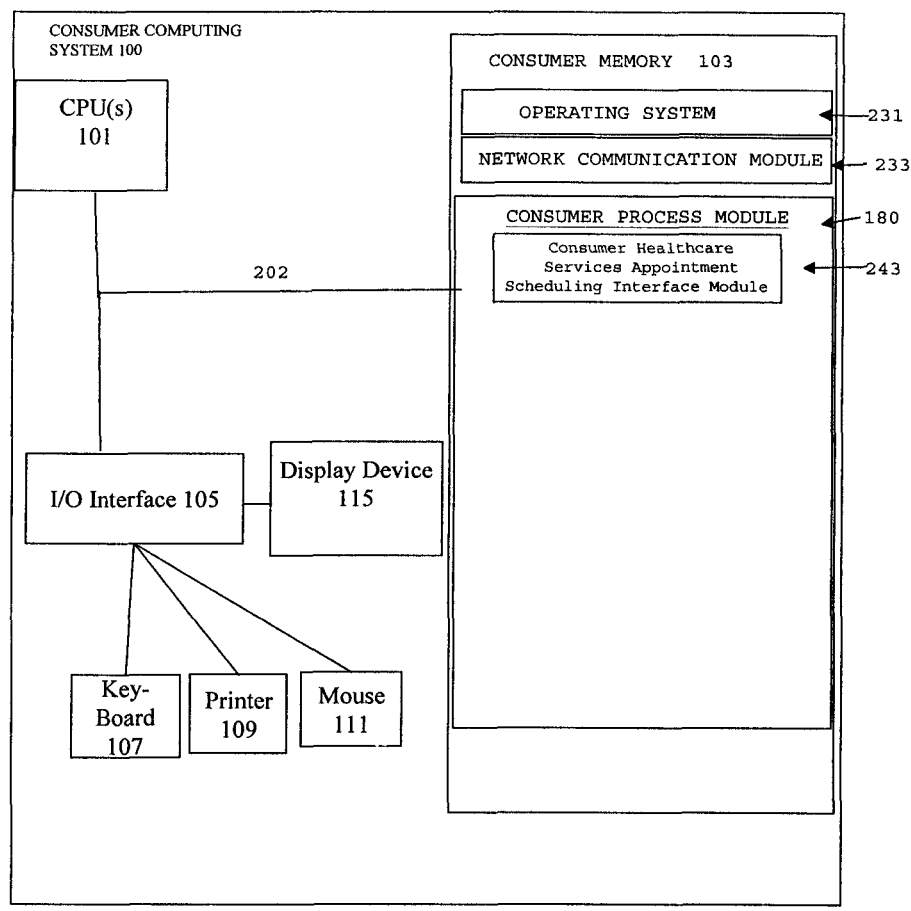
FIG. 2 is a block diagram showing more detail of an exemplary consumer computing system in accordance with one embodiment.

FIG. 2 is a more detailed block diagram of an exemplary consumer computing system 100 (FIG. 1). As seen in FIG. 2, in one embodiment, consumer computing system 100 includes one of more Central Processing Unit(s), CPU(s) 101; consumer memory 103; an Input/Output interface, I/O interface 105, including one or more user interface devices such as display device 115, keyboard 107, printer 109, and/or mouse 111; all interconnected by one or more communication buses 202.

As also seen in FIG. 2, in one embodiment, consumer memory 103 can store data and/or instructions associated with, but not limited to, the following elements, subsets of elements, and/or super sets of elements for processing by one or more processors, such as CPU(s) 101 (FIG. 2) and/or 151 (FIG. 3): operating system 231 that includes procedures, data, and/or instructions for handling various services and performing/coordinating hardware dependent tasks; network communications module 233 that includes procedures, data, and/or instructions, for connecting consumer computing system 100 to other computing systems, such as another consumer computing system 100 and/or provider computing system 150 of FIG. 1, and/or a network, such as network 130 of FIG. 1, and/or a database, such as databases 170/175 of FIG. 1; and consumer process module 180 (FIG. 2) that includes procedures, data, and/or instructions, for implementing at least part of a process for providing healthcare service appointment time and cost estimates at the time of scheduling 400 (FIG. 4).

As also seen in FIG. 2, in one embodiment, consumer process module 180 of consumer memory 103 includes consumer healthcare services appointment scheduling interface module 243 that includes procedures, data, and/or instructions for allowing a healthcare consumer to schedule a healthcare service appointment remotely using consumer computing system 100 and/or to respond to one or more screening questions.

Those of skill in the art will readily recognize that the choice of components, data, modules, and information shown in FIG. 2, the organization of the components, data, modules, and information shown in FIG. 2, and the manner of storage and location of storage of the data, modules, and information shown in FIG. 2 was made for illustrative purposes only and that other choices of components, data, modules, and information, organization of the components, data, modules, and information, manner of storing, and location of storage, of the data, modules, and information can be implemented without departing from the scope of the invention as set forth in the claims below. In particular, the various modules and/or data shown in FIG. 2 are illustrative only and not limiting. In various other embodiments, the particular modules and/or data shown in FIG. 2 can be grouped together in fewer modules and/or data locations or divided among more modules and/or data locations. Consequently, those of skill in the art will recognize that other orders and/or grouping are possible and the particular modules and/or data, order, and/or grouping shown in FIG. 2 and discussed herein do not limit the scope as claimed below.

A more detailed discussion of the operation of exemplary consumer computing system 100, consumer memory 103, and consumer process module 180 of consumer memory 103, is provided below with respect to FIG. 4.

Figure 3:
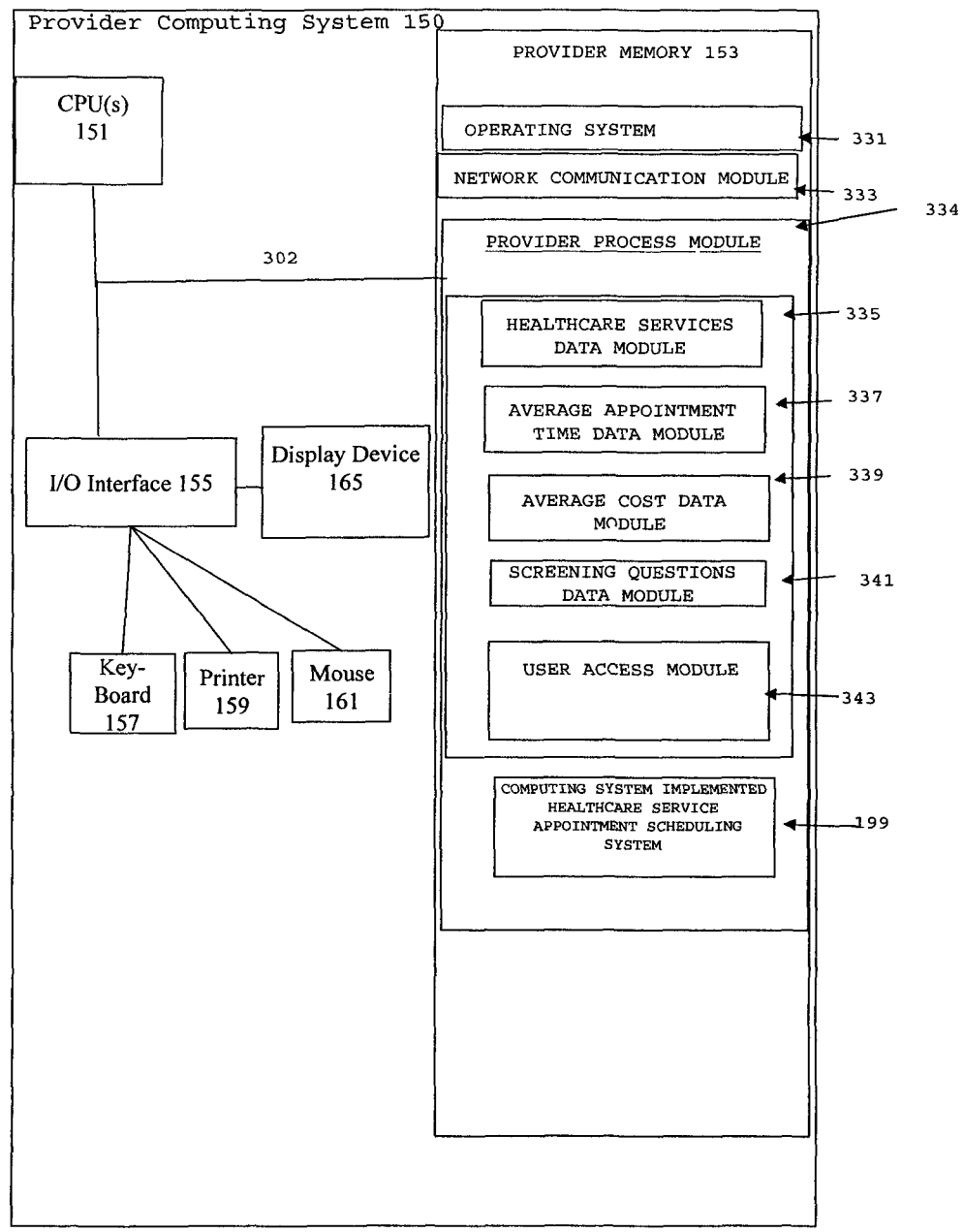
FIG. 3 is a block diagram showing more detail of an exemplary provider computing system in accordance with one embodiment.

FIG. 3 is a more detailed block diagram of an exemplary provider computing system 150. As seen in FIG. 3, in one embodiment, provider computing system 150 includes one of more Central Processing Unit(s), CPU(s) 151; provider memory 153; an Input/Output interface, I/O interface 155, including one or more user interface devices such as display device 165, keyboard 157, printer 159, and/or mouse 161; all interconnected by one or more communication buses 302.

As also seen in FIG. 3, in one embodiment, provider memory 153 can store data and/or instructions associated with, but not limited to, the following elements, subsets of elements, and/or super sets of elements for use in processing by one or more processors, such as CPU(s) 101 (FIG. 2) and/or 151 (FIG. 3): operating system 331 that includes procedures, data, and/or instructions for handling various services and performing/coordinating hardware dependent tasks; network communications module 333 that includes procedures, data, and/or instructions, for connecting provider computing system 150 to other computing systems, such as consumer computing system 100 and/or a network, such as network 130 of FIG. 1, and/or a database, such as databases 170/175 of FIG. 1; provider process module 334 (FIG. 3) that includes procedures, data, and/or instructions, for implementing at least part of a process for providing healthcare service appointment time and cost estimates at the time of scheduling 400 (FIG. 4); and computing system implemented healthcare service appointment scheduling system 199.

As also seen in FIG. 3, in one embodiment, provider process module 334 of provider memory 153 includes: healthcare services data module 335 that includes procedures, data, and/or instructions associated with one or more healthcare services provided by a given healthcare services provider and/or any standardized codes associated with one or more healthcare services provided by a given healthcare services provider; average appointment time data module 337 that includes procedures, data, and/or instructions associated with the average appointment time of one or more healthcare services provided by a given healthcare services provider; average cost data module 339 that includes procedures, data, and/or instructions associated with the average cost of one or more healthcare services provided by a given healthcare services provider; screening questions data module 341 that includes procedures, data, and/or instructions, associated with one or more screening questions to be asked a patient at the time of scheduling a healthcare service appointment; and access module 343 that includes procedures, data, and/or instructions associated with transferring data from one or more databases, such as databases 170 and/or 175 of FIG. 1, and/or screening questions data module 341, and/or healthcare services data module 335, and/or average appointment time data module 337, and/or average cost data module 339, and computing system implemented healthcare service appointment scheduling system 199.

Those of skill in the art will readily recognize that the choice of components, data, modules, and information shown in FIG. 3, the organization of the components, data, modules, and information shown in FIG. 3, and the manner of storage and location of storage of the data, modules, and information shown in FIG. 3 was made for illustrative purposes only and that other choices of components, data, modules, and information, organization of the components, data, modules, and information, manner of storing, and location of storage, of the data, modules, and information can be implemented without departing from the scope of the invention as set forth in the claims below. In particular, the various modules and/or data shown in FIG. 3 are illustrative only and not limiting. In various other embodiments, the particular modules and/or data shown in FIG. 3 can be grouped together in fewer modules and/or data locations or divided among more modules and/or data locations. Consequently, those of skill in the art will recognize that other orders and/or grouping are possible and the particular modules and/or data, order, and/or grouping shown in FIG. 3 and discussed herein do not limit the scope as claimed below.

A more detailed discussion of the operation of exemplary provider computing system 150, provider memory 153, and provider process module 334 of provider memory 153, is provided below with respect to FIG. 4.

Process

Herein, the terms "healthcare service consumer", "healthcare services consumer", "healthcare consumer" "service consumer" and "patient" and/or "consumer", are used to include any person, party, or parties, who receive healthcare services from a healthcare services provider, and/or an authorized agent of any person, party, or parties, who receive healthcare services from a healthcare services provider.

Herein, the term "healthcare service provider" and/or "healthcare services provider", and/or "healthcare provider" include any individual person, persons, agencies, institutions, organizations, businesses, and/or other entities that provide medical treatment, medications, therapy, advice, and/or equipment. For example, herein, the term "healthcare service provider" includes, but is not limited to: doctors; nurses; technicians; therapists; pharmacists; laboratories; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the terms "healthcare" and/or "healthcare service" include any general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; lab work, recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare service consumer's state of health.

Herein, the terms "healthcare insurance plan", "healthcare benefit plan", and "health insurance program" are used interchangeably to denote any policy, program, means and/or mechanism whereby a healthcare service consumer is provided healthcare benefits and/or healthcare services and/or entitlements to any from of healthcare.

Herein, the terms "healthcare insurance provider", "healthcare insurance service provider", "health insurance plan provider" and "health services insurance provider" are used interchangeably to denote any individual person, persons, agencies, institutions, organizations, businesses, and/or other entities that provide one or more healthcare insurance plans.

Herein, the terms "healthcare insurance plan administrator", "healthcare insurance service plan administrator", "health insurance plan administrator" and "health services insurance plan administrator" are used interchangeably to denote any individual person, persons, agencies, institutions, organizations, businesses, and/or other entities that administer and/or regulate and/or monitor one or more healthcare insurance plans.

As used herein, the term "computing system implemented data management system" includes, but is not limited to: computing system implemented appointment management systems, packages, programs, modules, or applications; computing system implemented personal and small business healthcare management systems, packages, programs, modules, or applications; computing system implemented personal and small business financial management systems, packages, programs, modules, or applications; computing system implemented business systems, packages, programs, modules, or applications; computing system implemented healthcare service provider office management systems, packages, programs, modules, or applications; computing system implemented payroll management systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented accounting and/or invoicing systems, packages, programs, modules, or applications; computing system implemented business and/or point of sale systems, packages, programs, modules, or applications; and various other electronic data driven data management systems, packages, programs, modules, or applications, whether known at the time of filling or as developed later.

As used herein, the term "computing system", includes, but is not limited to: a portable computer; a workstation; a two-way pager; a cellular telephone; a smart phone; a digital wireless telephone; a Personal Digital Assistant (PDA); a media player, i.e., an MP3 player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "network" includes, but is not limited to, any network or network system such as, but not limited to, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, whether available or known at the time of filing or as later developed.

As used herein, the term "database" includes, but is not limited to, any data storage mechanism known at the time of filing or as developed thereafter, such as, but not limited to: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based function. Herein, the term "database" can refer to any data storage means that is part of, or under the control of, any computing system, as defined herein, known at the time of filing, or as developed thereafter.

In accordance with one embodiment, a method and system for providing healthcare service appointment time and cost estimates at the time of scheduling includes a process for providing healthcare service appointment time and cost estimates at the time of scheduling whereby, in one embodiment, a healthcare services database is created that includes: data indicating any standardized codes associated with one or more healthcare services; data indicating the average appointment time associated with the one or more healthcare services; data indicating the average cost of the one or more healthcare services. In one embodiment data representing one or more screening questions to be asked a patient at the time of scheduling a healthcare service appointment is generated. In one embodiment, the one or more screening questions to be asked a patient at the time of scheduling a healthcare service appointment are chosen such that the patient's response to the one or more questions indicates which, if any, of the one or more healthcare services in the healthcare services database may be needed by the patient at the healthcare services appointment. In one embodiment, the data in the healthcare services database is then used to determine any standardized codes associated with the needed healthcare service, the average appointment time associated with the needed healthcare service, and/or the average cost of the needed healthcare service. The patient is then scheduled for a healthcare service appointment having an allocated time based on the average appointment time associated with the needed healthcare service and/or the patient is provided an estimate of the cost of the healthcare service appointment based on the average cost of the needed healthcare service appointment, in one embodiment, at the time the healthcare service appointment is scheduled.

FIG. 4 a flow chart depicting a process for providing healthcare service appointment time and cost estimates at the time of scheduling 400 in accordance with one embodiment.

In one embodiment, process for providing healthcare service appointment time and cost estimates at the time of scheduling 400 is a stand alone system implemented on, or accessed through, a computing system, such as computing systems 100 and/or 150 of FIGS. 1, 2, and/or 3.

In one embodiment, process for providing healthcare service appointment time and cost estimates at the time of scheduling 400 is part of, accessible by, or otherwise associated with, a computing system implemented data management system, such as any computing system implemented data management system discussed herein, and/or known in the art at the time of filing, and/or as developed after the time of filing. In one embodiment, process for providing healthcare service appointment time and cost estimates at the time of scheduling 400 is part of, accessible by, or otherwise associated with, a computing system implemented healthcare service appointment scheduling system, such as computing system implemented healthcare service appointment scheduling system 199. In one embodiment, process for providing healthcare service appointment time and cost estimates at the time of scheduling 400 is part of, accessible by, or otherwise associated with, a computing system implemented healthcare management system.

Process for providing healthcare service appointment time and cost estimates at the time of scheduling 400 begins at ENTER OPERATION 401 of FIG. 4 and process flow proceeds to OBTAIN DATA INDICATING HEALTHCARE SERVICES PROVIDED BY A GIVEN HEALTHCARE SERVICE PROVIDER OPERATION 403.

In one embodiment, at OBTAIN DATA INDICATING HEALTHCARE SERVICES PROVIDED BY A GIVEN HEALTHCARE SERVICE PROVIDER OPERATION 403, data indicating one or more healthcare services provided by a given healthcare service provider is obtained by process for providing healthcare service appointment time and cost estimates at the time of scheduling 400.

In one embodiment, at OBTAIN DATA INDICATING HEALTHCARE SERVICES PROVIDED BY A GIVEN HEALTHCARE SERVICE PROVIDER OPERATION 403, the data indicating one or more healthcare services provided by the given healthcare service provider is obtained by asking the given healthcare service provider for the information and then entering the information as data into a computing system memory, such as any computing system memory discussed herein, and/or known in the art at the time of filing, and/or as developed after the time of filing, associated with any computing system, such as any computing system discussed herein, and/or known in the art at the time of filing, and/or as developed after the time of filing.

In one embodiment, at OBTAIN DATA INDICATING HEALTHCARE SERVICES PROVIDED BY A GIVEN HEALTHCARE SERVICE PROVIDER OPERATION 403, the data indicating one or more healthcare services provided by the given healthcare service provider is obtained by analyzing the healthcare service provider's records and then transferring, or otherwise entering, the information as data into a computing system memory, such as any computing system memory discussed herein, and/or known in the art at the time of filing, and/or as developed after the time of filing, associated with any computing system, such as any computing system discussed herein, and/or known in the art at the time of filing, and/or as developed after the time of filing.

In one embodiment, at OBTAIN DATA INDICATING HEALTHCARE SERVICES PROVIDED BY A GIVEN HEALTHCARE SERVICE PROVIDER OPERATION 403, the data indicating one or more healthcare services provided by the given healthcare service provider is obtained by analyzing a healthcare insurance provider's records and then transferring, or otherwise entering, the information as data into a computing system memory, such as any computing system memory discussed herein, and/or known in the art at the time of filing, and/or as developed after the time of filing, associated with any computing system, such as any computing system discussed herein, and/or known in the art at the time of filing, and/or as developed after the time of filing.

In one embodiment, at OBTAIN DATA INDICATING HEALTHCARE SERVICES PROVIDED BY A GIVEN HEALTHCARE SERVICE PROVIDER OPERATION 403, the data indicating one or more healthcare services provided by the given healthcare service provider is determined based on one or more areas of practice associated with the healthcare services provider and then transferring, or otherwise entering, the information as data into a computing system memory, such as any computing system memory discussed herein, and/or known in the art at the time of filing, and/or as developed after the time of filing, associated with any computing system, such as any computing system discussed herein, and/or known in the art at the time of filing, and/or as developed after the time of filing.

In some embodiments, at OBTAIN DATA INDICATING HEALTHCARE SERVICES PROVIDED BY A GIVEN HEALTHCARE SERVICE PROVIDER OPERATION 403, the data indicating one or more healthcare services provided by the given healthcare service provider is obtained from any source of the data indicating one or more healthcare services provided by the given healthcare service provider, as discussed herein, and/or as known in the art at the time of filing, and/or as developed after the time of filing.

In one embodiment, once data indicating one or more healthcare services provided by the given healthcare service provider is obtained by process for providing healthcare service appointment time and cost estimates at the time of scheduling 400 at OBTAIN DATA INDICATING HEALTHCARE SERVICES PROVIDED BY A GIVEN HEALTHCARE SERVICE PROVIDER OPERATION 403, process flow proceeds to DETERMINE ANY STANDARDIZED CODES ASSOCIATED WITH ONE OR MORE OF THE HEALTHCARE SERVICES OPERATION 405.

In one embodiment, at DETERMINE ANY STANDARDIZED CODES ASSOCIATED WITH ONE OR MORE OF THE HEALTHCARE SERVICES OPERATION 405 data indicating any standardized codes associated with the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider.

In one embodiment, the standardized codes of DETERMINE ANY STANDARDIZED CODES ASSOCIATED WITH ONE OR MORE OF THE HEALTHCARE SERVICES OPERATION 405 are codes generated and/or used by professional associations, such as the American Medical Association (AMA). For instance, in one embodiment, AMA provided CPT codes indicating defined medical procedures are used and correlated to the one or more healthcare services provided by the given healthcare service provider of OBTAIN DATA INDICATING HEALTHCARE SERVICES PROVIDED BY A GIVEN HEALTHCARE SERVICE PROVIDER OPERATION 403. Likewise, in one embodiment, ICD9 codes from the AMA indicating defined diagnoses are used and correlated to the one or more healthcare services provided by the given healthcare service provider of OBTAIN DATA INDICATING HEALTHCARE SERVICES PROVIDED BY A GIVEN HEALTHCARE SERVICE PROVIDER OPERATION 403.

In other embodiments, the standardized codes of DETERMINE ANY STANDARDIZED CODES ASSOCIATED WITH ONE OR MORE OF THE HEALTHCARE SERVICES OPERATION 405 are other codes provided by other organizations such as, but not limited to, healthcare insurance provider codes, codes used by a healthcare service provider, or codes used by a government agency.

In other embodiments, the standardized codes of DETERMINE ANY STANDARDIZED CODES ASSOCIATED WITH ONE OR MORE OF THE HEALTHCARE SERVICES OPERATION 405 are any standardized codes associated with the one or more healthcare services provided by the given healthcare service provider as discussed herein, and/or as known in the art at the time of filing, and/or as developed after the time of filing, and are obtained from any source of these codes as discussed herein, and/or as known in the art at the time of filing, and/or as developed after the time of filing.

In one embodiment, once data indicating any standardized codes associated with the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider at DETERMINE ANY STANDARDIZED CODES ASSOCIATED WITH ONE OR MORE OF THE HEALTHCARE SERVICES OPERATION 405, process flow proceeds to DETERMINE AN AVERAGE APPOINTMENT TIME ASSOCIATED WITH ONE OR MORE OF THE HEALTHCARE SERVICES OPERATION 407.

In one embodiment, at DETERMINE AN AVERAGE APPOINTMENT TIME ASSOCIATED WITH ONE OR MORE OF THE HEALTHCARE SERVICES OPERATION 407 data indicating the average appointment time associated with the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider.

In one embodiment, at DETERMINE AN AVERAGE APPOINTMENT TIME ASSOCIATED WITH ONE OR MORE OF THE HEALTHCARE SERVICES OPERATION 407 the average appointment time associated with the one or more healthcare services provided by the given healthcare service provider is determined based on, and/or using, the standardized codes associated with the one or more healthcare services provided by the given healthcare service provider of DETERMINE ANY STANDARDIZED CODES ASSOCIATED WITH ONE OR MORE OF THE HEALTHCARE SERVICES OPERATION 405.

In one embodiment, at DETERMINE AN AVERAGE APPOINTMENT TIME ASSOCIATED WITH ONE OR MORE OF THE HEALTHCARE SERVICES OPERATION 407 the average appointment time associated with the one or more healthcare services provided by the given healthcare service provider is determined based on analysis of the healthcare service provider's records.

In one embodiment, at DETERMINE AN AVERAGE APPOINTMENT TIME ASSOCIATED WITH ONE OR MORE OF THE HEALTHCARE SERVICES OPERATION 407, the average appointment time associated with the one or more healthcare services provided by the given healthcare service provider is determined based on analysis of a healthcare insurance provider's records.

In some embodiments, at DETERMINE AN AVERAGE APPOINTMENT TIME ASSOCIATED WITH ONE OR MORE OF THE HEALTHCARE SERVICES OPERATION 407 the average appointment time associated with the one or more healthcare services provided by the given healthcare service provider is determined based on analysis of any data from any source of data indicating the average appointment time associated with the one or more healthcare services provided by the given healthcare service provider as discussed herein, and/or as known in the art at the time of filing, and/or as developed after the time of filing.

In one embodiment, once data indicating the average appointment time associated with the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider at DETERMINE AN AVERAGE APPOINTMENT TIME ASSOCIATED WITH ONE OR MORE OF THE HEALTHCARE SERVICES OPERATION 407, process flow proceeds to DETERMINE AN AVERAGE COST ASSOCIATED WITH ONE OR MORE OF THE HEALTHCARE SERVICES OPERATION 409.

In one embodiment, at DETERMINE AN AVERAGE COST ASSOCIATED WITH ONE OR MORE OF THE HEALTHCARE SERVICES OPERATION 409, data indicating the average cost of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider.

In one embodiment, at DETERMINE AN AVERAGE COST ASSOCIATED WITH ONE OR MORE OF THE HEALTHCARE SERVICES OPERATION 409, the average cost of the one or more healthcare services provided by the given healthcare service provider is determined based on, and/or using, the standardized codes associated with the one or more healthcare services provided by the given healthcare service provider of DETERMINE ANY STANDARDIZED CODES ASSOCIATED WITH ONE OR MORE OF THE HEALTHCARE SERVICES OPERATION 405.

In one embodiment, at DETERMINE AN AVERAGE COST ASSOCIATED WITH ONE OR MORE OF THE HEALTHCARE SERVICES OPERATION 409, the average cost of the one or more healthcare services provided by the given healthcare service provider is determined based on analysis of the healthcare service provider's records.

In one embodiment, at DETERMINE AN AVERAGE COST ASSOCIATED WITH ONE OR MORE OF THE HEALTHCARE SERVICES OPERATION 409, the average cost of the one or more healthcare services provided by the given healthcare service provider is determined based on analysis of a healthcare insurance provider's records.

In some embodiments, at DETERMINE AN AVERAGE COST ASSOCIATED WITH ONE OR MORE OF THE HEALTHCARE SERVICES OPERATION 409, the average cost of the one or more healthcare services provided by a given healthcare service provider is determined based on analysis of any data from any source of data indicating the average cost of the one or more healthcare services provided by the given healthcare service provider as discussed herein, and/or as known in the art at the time of filing, and/or as developed after the time of filing.

In one embodiment, once data indicating the average cost of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 is obtained and correlated to the respective one or more healthcare services provided by the given healthcare service provider at DETERMINE AN AVERAGE COST ASSOCIATED WITH ONE OR MORE OF THE HEALTHCARE SERVICES OPERATION 409, process flow proceeds to FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 a healthcare services database is created that includes: the data indicating any standardized codes associated with one or more healthcare services of DETERMINE ANY STANDARDIZED CODES ASSOCIATED WITH ONE OR MORE OF THE HEALTHCARE SERVICES OPERATION 405; the data indicating the average appointment time associated with the one or more healthcare services DETERMINE AN AVERAGE APPOINTMENT TIME ASSOCIATED WITH ONE OR MORE OF THE HEALTHCARE SERVICES OPERATION 407; and the data indicating the average cost of the one or more healthcare services DETERMINE AN AVERAGE COST ASSOCIATED WITH ONE OR MORE OF THE HEALTHCARE SERVICES OPERATION 409.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in any database, such as databases 170 and/or 175 of FIG. 1.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in a healthcare services database, that is any database, such as database 170 of FIG. 1.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in one or more memory systems, databases, cache memories, and/or any main memory or mass memory, associated with a provider computing system, and/or in any computing system and/or server system, or other device, in another location, or on/in a computer readable medium, and/or any other computer program product, as defined herein, and/or known in the art at the time of filing, and/or as developed after the time of filing.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider is stored in whole, or in part, on a webpage, in a web-based system, or on a public network such as the Internet.

For instance, in one embodiment, In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in whole, or in part, in a data storage means maintained by, accessible by, owned by, or otherwise related to: process for providing healthcare service appointment time and cost estimates at the time of scheduling 400 (FIG. 4), and/or a provider of process for providing healthcare service appointment time and cost estimates at the time of scheduling 400; or any other party, by any one of the numerous mechanisms known to those of skill in the art.

In one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in a memory system, such as provider memory system 153 of provider computing system 150 (FIG. 1 and/or FIG. 3), in various memory modules, such as healthcare services data module 335, average appointment time data module 337, and average cost data module 341, of provider process module 334 of provider memory 153 of provider computing system 150 (FIG. 3).

Returning to FIG. 4, in one embodiment, at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411: the data indicating any standardized codes associated with the one or more healthcare services provided by the given healthcare service provider; the data indicating the average appointment time associated with one or more healthcare services provided by the given healthcare service provider; and the data indicating the cost of the one or more healthcare services provided by the given healthcare service provider is correlated, and/or associated with, the respective one or more healthcare services provided by the given healthcare service provider and stored in whole, or in part, in any computing system memory, or server memory system memory, or database, such as databases 170/175, of FIG. 1, or in a cache memory, such as cache memory 153A of FIG. 1 and FIG. 3, or in any main memory or mass memory, associated with a computing system, such as computing systems 100 or 150 described above. In one embodiment, the data, in whole, or in part, is stored in any computing system and/or server system, or other device, in another location, or on/in a computer readable medium, and/or any other computer program product. In one embodiment, the data, in whole, or in part, is stored on a webpage, in a web-based system, or on a public network such as the Internet.

In one embodiment, once a healthcare services database is created that includes: the data indicating any standardized codes associated with one or more healthcare services of DETERMINE ANY STANDARDIZED CODES ASSOCIATED WITH ONE OR MORE OF THE HEALTHCARE SERVICES OPERATION 405; the data indicating the average appointment time associated with the one or more healthcare services DETERMINE AN AVERAGE APPOINTMENT TIME ASSOCIATED WITH ONE OR MORE OF THE HEALTHCARE SERVICES OPERATION 407; and the data indicating the average cost of the one or more healthcare services DETERMINE AN AVERAGE COST ASSOCIATED WITH ONE OR MORE OF THE HEALTHCARE SERVICES OPERATION 409 at FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411, process flow proceeds to GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413.

In one embodiment, at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 one or more screening questions to be asked a patient at the time of scheduling a healthcare service appointment are generated such that the patient's response to the one or more questions indicates which, if any, of the one or more healthcare services in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 may be needed by the patient at the healthcare services appointment.

In one embodiment, at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 the one or more screening questions to be asked a patient at the time of scheduling a healthcare service appointment are chosen and/or generated by the provider of process for providing healthcare service appointment time and cost estimates at the time of scheduling 400.

In one embodiment, at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 the one or more screening questions to be asked a patient at the time of scheduling a healthcare service appointment are chosen and/or generated by the healthcare service provider.

In one embodiment, at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 the one or more screening questions to be asked a patient at the time of scheduling a healthcare service appointment are chosen and/or generated by the provider of process for providing healthcare service appointment time and cost estimates at the time of scheduling 400 and are editable by the healthcare service provider.

As noted above, in one embodiment, at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 the one or more screening questions to be asked a patient at the time of scheduling a healthcare service appointment are chosen such that the patient's response to the one or more screening questions to be asked a patient at the time of scheduling a healthcare service appointment indicates which, if any, of the one or more healthcare services provided by the given healthcare service provider in the healthcare services database may be needed by the patient at the healthcare service appointment.

For instance, in one embodiment, the one or more screening questions to be asked a patient at the time of scheduling a healthcare service appointment of at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 request information regarding the patient's current symptoms and/or condition.

As another example, in one embodiment, the one or more screening questions to be asked a patient at the time of scheduling a healthcare service appointment of at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 request information regarding the patient's medical history and/or known conditions.

As another example, in one embodiment, the one or more screening questions to be asked a patient at the time of scheduling a healthcare service appointment of at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 request information regarding the patient's previous appointments with the healthcare service provider and/or if the patient has scheduled this type of healthcare service appointment before.

As another example, in one embodiment, the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 request information regarding the patient's healthcare insurance coverage.

In other embodiments, the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 request any information regarding the patient's health and/or healthcare status that the provider of process for providing healthcare service appointment time and cost estimates at the time of scheduling 400, and/or the healthcare service provider, determines may help associate the appointment being scheduled with any of the one or more healthcare services provided by a given healthcare service provider in the healthcare services database.

In one embodiment, once one or more screening questions to be asked a patient at the time of scheduling a healthcare service appointment are generated such that the patient's response to the one or more questions indicates which, if any, of the one or more healthcare services in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 may be needed by the patient at the healthcare services appointment at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413, process flow proceeds to STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in a screening questions database that may, or may not, be the same database as the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in any database, such as databases 170 and/or 175 of FIG. 1.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in a screening questions database, that is any database such as database 175 of FIG. 1.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in one or more memory systems, databases, cache memories, and/or any main memory or mass memory, associated with a provider computing system, and/or in any computing system and/or server system, or other device, in another location, or on/in a computer readable medium, and/or any other computer program product, as defined herein, and/or known in the art at the time of filing, and/or as developed after the time of filing.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in whole, or in part, on a webpage, in a web-based system, or on a public network such as the Internet.

For instance, in one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in whole, or in part, in a data storage means maintained by, accessible by, owned by, or otherwise related to: process for providing healthcare service appointment time and cost estimates at the time of scheduling 400 (FIG. 4), and/or a provider of process for providing healthcare service appointment time and cost estimates at the time of scheduling 400; or any other party, by any one of the numerous mechanisms known to those of skill in the art.

In one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in a memory system, such as provider memory system 153 of provider computing system 150 (FIG. 1 and/or FIG. 3), in various memory modules, such as screening questions data module 341 of provider process module 334 of provider memory 153 of provider computing system 150 (FIG. 3).

Returning to FIG. 4, in one embodiment, at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in whole, or in part, in any computing system memory, or server memory system memory, or database, such as databases 170/175, of FIG. 1, or in a cache memory, such as cache memory 153A of FIG. 1 and FIG. 3, or in any main memory or mass memory, associated with a computing system, such as computing systems 100 or 150 described above. In one embodiment, the data, in whole, or in part, is stored in any computing system and/or server system, or other device, in another location, or on/in a computer readable medium, and/or any other computer program product. In one embodiment, the data, in whole, or in part, is stored on a webpage, in a web-based system, or on a public network such as the Internet.

In one embodiment, once the data representing the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 is stored in a screening questions database that may, or may not, be the same database as the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 at STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415, process flow proceeds to PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417.

In one embodiment, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 a computing system implemented healthcare service appointment scheduling system, such as computing system implemented healthcare service appointment scheduling system 199 of FIG. 1, is provided and the computing system implemented healthcare service appointment scheduling system is provided access to the data in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 and/or the screening questions database of STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415.

In one embodiment, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 the computing system implemented healthcare service appointment scheduling system is provided access to process for providing healthcare service appointment time and cost estimates at the time of scheduling 400 and/or the data in the healthcare services database and/or the screening questions database, but the computing system implemented healthcare service appointment scheduling system is independent of process for providing healthcare service appointment time and cost estimates at the time of scheduling 400.

In one embodiment, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 the computing system implemented healthcare service appointment scheduling system is provided access to process for providing healthcare service appointment time and cost estimates at the time of scheduling 400 and/or the data in the healthcare services database and/or the screening questions database via a website and/or any network, as discussed herein, and/or as known in the art at the time of filing, and/or as developed after the time of filing.

In one embodiment, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 the computing system implemented healthcare service appointment scheduling system is provided access to process for providing healthcare service appointment time and cost estimates at the time of scheduling 400 and/or the data in the healthcare services database and/or the screening questions database by providing the computing system implemented healthcare service appointment scheduling system access to a computing system, and/or a server system, under the control of one or more healthcare service providers, and/or any third party.

In one embodiment, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 the computing system implemented healthcare service appointment scheduling system is provided access to process for providing healthcare service appointment time and cost estimates at the time of scheduling 400 and/or the data in the healthcare services database and/or the screening questions database using a computer program product as discussed herein, and/or as known in the art at the time of filing, and/or as developed after the time of filing.

In other embodiments, at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 the computing system implemented healthcare service appointment scheduling system is provided access to process for providing healthcare service appointment time and cost estimates at the time of scheduling 400 and/or the data in the healthcare services database and/or the screening questions database using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, once a computing system implemented healthcare service appointment scheduling system, such as computing system implemented healthcare service appointment scheduling system 199 of FIG. 1, is provided and the computing system implemented healthcare service appointment scheduling system is provided access to the data in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 and/or the screening questions database of STORE THE DATA REPRESENTING THE ONE OR MORE SCREENING QUESTIONS TO BE ASKED OF A PATIENT AT THE TIME OF SCHEDULING A HEALTHCARE SERVICE APPOINTMENT OPERATION 415 at PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417, process flow proceeds to WHEN SCHEDULING A HEALTHCARE SERVICES APPOINTMENT FOR A PATIENT ASK THE PATIENT THE ONE OR MORE SCREENING QUESTIONS OPERATION 419.

In one embodiment, at WHEN SCHEDULING A HEALTHCARE SERVICES APPOINTMENT FOR A PATIENT ASK THE PATIENT THE ONE OR MORE SCREENING QUESTIONS OPERATION 419 when the computing system implemented healthcare service appointment scheduling system of PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 is being used to schedule a given healthcare service appointment for a given patient, the given patient is asked the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413.

In one embodiment, at WHEN SCHEDULING A HEALTHCARE SERVICES APPOINTMENT FOR A PATIENT ASK THE PATIENT THE ONE OR MORE SCREENING QUESTIONS OPERATION 419 when the computing system implemented healthcare service appointment scheduling system of PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 is being used to schedule a follow-up, or additional procedure and/or analysis associated with a given healthcare service appointment for a given patient, the given patient is asked the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413.

As noted above, in one embodiment the healthcare consumer is provided the ability to schedule a healthcare service appointment remotely using consumer computing system 100 (FIGS. 1 and 2) and/or to respond to one or more screening questions. In addition, in one embodiment, the healthcare consumer is provided the ability to schedule a healthcare service appointment using a provider computing system, such as provider computing system 150 (FIGS. 1 and 3) and/or to respond to one or more screening questions. Returning to FIG. 4, in one embodiment, at WHEN SCHEDULING A HEALTHCARE SERVICES APPOINTMENT FOR A PATIENT ASK THE PATIENT THE ONE OR MORE SCREENING QUESTIONS OPERATION 419 the given patient is asked the one or more screening questions to be asked a patient at the time of scheduling a healthcare service appointment via a "wizard" such as an appointment "scheduling wizard" that appears on a display device, such as display device 115 of consumer computing system 100 of FIG. 2, and/or display device 165 of provider computing system 150 of FIG. 3, the requests responses to the one or more screening questions to be asked a patient at the time of scheduling a healthcare service appointment via pop-up windows and/or data entry fields via a user interface device such as, but not limited to: a keyboard; such as keyboards 107, 159 of FIG. 2/FIG. 3; a mouse, such as mice 111/161 of FIG. 2/FIG. 3; a touchpad; voice recognition software; or any other device and/or system capable of providing user input to a computing system and/or for translating user actions into computing system operations, whether available or known at the time of filing or as developed later.

In one embodiment, at WHEN SCHEDULING A HEALTHCARE SERVICES APPOINTMENT FOR A PATIENT ASK THE PATIENT THE ONE OR MORE SCREENING QUESTIONS OPERATION 419, the given patient is asked the one or more screening questions to be asked a patient at the time of scheduling a healthcare service appointment via an automated phone response system.

In one embodiment, at WHEN SCHEDULING A HEALTHCARE SERVICES APPOINTMENT FOR A PATIENT ASK THE PATIENT THE ONE OR MORE SCREENING QUESTIONS OPERATION 419, the given patient is asked the one or more screening questions to be asked a patient at the time of scheduling a healthcare service appointment via questions asked by an employee of, or agent for, the healthcare services provider over the phone.

In one embodiment, at WHEN SCHEDULING A HEALTHCARE SERVICES APPOINTMENT FOR A PATIENT ASK THE PATIENT THE ONE OR MORE SCREENING QUESTIONS OPERATION 419, the given patient is asked the one or more screening questions to be asked a patient at the time of scheduling a healthcare service appointment via questions asked by an employee of, or agent for, the healthcare services provider in person.

In other embodiments, at WHEN SCHEDULING A HEALTHCARE SERVICES APPOINTMENT FOR A PATIENT ASK THE PATIENT THE ONE OR MORE SCREENING QUESTIONS OPERATION 419 the given patient is asked the one or more screening questions to be asked a patient at the time of scheduling a healthcare service appointment via any means, mechanism, and/or process for asking, and receiving responses to, the one or more screening questions to be asked a patient at the time of scheduling a healthcare service appointment discussed herein, and/or as known in the art at the time of filing, and/or as developed after the time of filing.

As noted above, in one embodiment, the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 are chosen such that the patient's response to the one or more screening questions to be asked a patient at the time of scheduling a healthcare service appointment indicates which, if any, of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 may be needed by the given patient at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419.

Therefore, in one embodiment, based on the given patient's responses to the one or more screening questions to be asked a patient at the time of scheduling a healthcare service appointment at least one of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is identified as being required at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419.

In one embodiment, once the computing system implemented healthcare service appointment scheduling system of PROVIDE A COMPUTING SYSTEM IMPLEMENTED HEALTHCARE SERVICES APPOINTMENT SCHEDULING SYSTEM ACCESS TO THE DATA REPRESENTING THE ONE OR MORE SCREENING QUESTIONS OPERATION 417 is used to schedule a given healthcare service appointment for a given patient, and the given patient is asked the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 at WHEN SCHEDULING A HEALTHCARE SERVICES APPOINTMENT FOR A PATIENT ASK THE PATIENT THE ONE OR MORE SCREENING QUESTIONS OPERATION 419, process flow proceeds to USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421.

In one embodiment, at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421 based on the given patient's responses to the one or more screening questions to be asked a patient at the time of scheduling a healthcare service appointment at least one of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is identified as being required at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419.

As noted above, in one embodiment, the one or more screening questions to be asked a patient at the time of scheduling a healthcare service appointment of GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413 are chosen such that the patient's response to the one or more screening questions to be asked a patient at the time of scheduling a healthcare service appointment indicates which, if any, of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 may be needed by the given patient at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419.

Therefore, in one embodiment, using the given patient's responses to the one or more screening questions to be asked a patient at the time of scheduling a healthcare service appointment, at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421 a search of the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is conducted to find at least one of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database that is required at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419.

In one embodiment, once based on the given patient's responses to the one or more screening questions to be asked a patient at the time of scheduling a healthcare service appointment at least one of the one or more healthcare services provided by the given healthcare service provider of OBTAIN DATA INDICATING HEALTHCARE SERVICES PROVIDED BY A GIVEN HEALTHCARE SERVICE PROVIDER OPERATION 403 in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is identified as being required at the given healthcare service appointment being scheduled at WHEN SCHEDULING A HEALTHCARE SERVICES APPOINTMENT FOR A PATIENT ASK THE PATIENT THE ONE OR MORE SCREENING QUESTIONS OPERATION 419 at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421, process flow proceeds to USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423 the data in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is used to schedule a given healthcare service appointment for the given patient having an allocated time based on the average appointment time associated with the needed healthcare service determined using the data of DETERMINE AN AVERAGE APPOINTMENT TIME ASSOCIATED WITH ONE OR MORE OF THE HEALTHCARE SERVICES OPERATION 407 and/or the patient is provided an estimate of the cost of the healthcare service appointment based on the average cost of the needed healthcare service appointment determined using the data of DETERMINE AN AVERAGE COST ASSOCIATED WITH ONE OR MORE OF THE HEALTHCARE SERVICES OPERATION 409, all in one embodiment, at the time the healthcare service appointment is scheduled at WHEN SCHEDULING A HEALTHCARE SERVICES APPOINTMENT FOR A PATIENT ASK THE PATIENT THE ONE OR MORE SCREENING QUESTIONS OPERATION 419.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, once the healthcare service required at the given healthcare service appointment is identified at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421, the data in the healthcare services database, including the data of DETERMINE ANY STANDARDIZED CODES ASSOCIATED WITH ONE OR MORE OF THE HEALTHCARE SERVICES OPERATION 405, is used to determine any standardized codes associated with the healthcare service required at the given healthcare service appointment.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, once the healthcare service required at the given healthcare service appointment is identified at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421, the data in the healthcare services database, including the data of DETERMINE ANY STANDARDIZED CODES ASSOCIATED WITH ONE OR MORE OF THE HEALTHCARE SERVICES OPERATION 405, and/or the data of DETERMINE AN AVERAGE APPOINTMENT TIME ASSOCIATED WITH ONE OR MORE OF THE HEALTHCARE SERVICES OPERATION 407, is used to determine the average amount of time required for healthcare service appointments involving the healthcare service required by the given patient at the given healthcare service appointment of USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, the given patient is then scheduled for the given healthcare service appointment and the given healthcare service appointment is allocated an amount of time based on the average amount of time required for healthcare service appointments involving the healthcare service required at the given healthcare service appointment.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, once the healthcare service required at the given healthcare service appointment is identified at USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421, the data in the healthcare services database, including the data of DETERMINE ANY STANDARDIZED CODES ASSOCIATED WITH ONE OR MORE OF THE HEALTHCARE SERVICES OPERATION 405, and/or the data of DETERMINE AN AVERAGE COST ASSOCIATED WITH ONE OR MORE OF THE HEALTHCARE SERVICES OPERATION 409, is used to determine the average cost for the healthcare service required by the given patient at the given healthcare service appointment USE THE PATIENT RESPONSES TO THE SCREENING QUESTIONS TO DETERMINE WHICH OF THE ONE OR MORE HEALTHCARE SERVICES IN THE HEALTHCARE SERVICES DATABASE THE PATIENT REQUIRES OPERATION 421.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained from the patient's healthcare insurance provider and/or a database or data source associated with the patient's healthcare insurance provider.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained from the patient's responses to the one or more screening questions to be asked a patient at the time of scheduling a healthcare service appointment at GENERATE DATA REPRESENTING ONE OR MORE SCREENING QUESTIONS TO BE ASKED OF A PATIENT AT THE TIME OF SCHEDULING A HEALTHCARE SERVICE APPOINTMENT OPERATION 413.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained from analysis of the healthcare service provider's records.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained from an analysis of the patient's healthcare records.

In some embodiments, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, data regarding the patient's healthcare insurance coverage is obtained from, and/or determined based on analysis of any data from, any source of data indicating the patient's healthcare insurance coverage as discussed herein, and/or as known in the art at the time of filing, and/or as developed after the time of filing.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, the data in the healthcare services database, including the data of DETERMINE ANY STANDARDIZED CODES ASSOCIATED WITH ONE OR MORE OF THE HEALTHCARE SERVICES OPERATION 405, and/or the data of DETERMINE AN AVERAGE COST ASSOCIATED WITH ONE OR MORE OF THE HEALTHCARE SERVICES OPERATION 409, and the data regarding the patient's healthcare insurance coverage, is used to estimate the given patient's out-of-pocket costs for the given healthcare service appointment at the time the given healthcare service appointment is scheduled.

In one embodiment, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, the patient is provided the opportunity to pre-pay all, or part, of the estimated out-of-pocket costs for the given healthcare service appointment at the time the given healthcare service appointment is scheduled.

In one embodiment, once the data in the healthcare services database of FOR THE ONE OR MORE HEALTHCARE SERVICES, CORRELATE AND STORE IN A HEALTHCARE SERVICES DATABASE DATA INDICATING: THE CODES ASSOCIATED WITH THE HEALTHCARE SERVICE; THE APPOINTMENT TIME ASSOCIATED WITH THE HEALTHCARE SERVICE; AND THE COST ASSOCIATED WITH THE HEALTHCARE SERVICE OPERATION 411 is used to schedule a given healthcare service appointment for the given patient having an allocated time based on the average appointment time associated with the needed healthcare service determined using the data of DETERMINE AN AVERAGE APPOINTMENT TIME ASSOCIATED WITH ONE OR MORE OF THE HEALTHCARE SERVICES OPERATION 407 and/or the patient is provided an estimate of the cost of the healthcare service appointment based on the average cost of the needed healthcare service appointment determined using the data of DETERMINE AN AVERAGE COST ASSOCIATED WITH ONE OR MORE OF THE HEALTHCARE SERVICES OPERATION 409, all in one embodiment, at the time the healthcare service appointment is scheduled at WHEN SCHEDULING A HEALTHCARE SERVICES APPOINTMENT FOR A PATIENT ASK THE PATIENT THE ONE OR MORE SCREENING QUESTIONS OPERATION 419, at USE THE DATA IN THE HEALTHCARE SERVICES DATABASE TO ESTIMATE HOW MUCH TIME TO SCHEDULE FOR THE PATIENT'S HEALTHCARE SERVICES APPOINTMENT AND/OR TO PROVIDE THE PATIENT AN ESTIMATE OF THE COST OF THE HEALTHCARE SERVICES APPOINTMENT AT THE TIME THE APPOINTMENT IS SCHEDULED OPERATION 423, process flow proceeds to EXIT OPERATION 430.

In one embodiment, at EXIT OPERATION 430, process for providing healthcare service appointment time and cost estimates at the time of scheduling 400 is exited to await new data.

In the discussion above, specific embodiments were presented wherein the patient was making a given healthcare services appointment. However, all, or part, of process for providing healthcare service appointment time and cost estimates at the time of scheduling 400, and the discussion above, is equally applicable to a situation where a patient is recommended a follow-up appointment and/or further analysis/testing at, or as a result of, a given healthcare services appointment. In theses instances, process for providing healthcare service appointment time and cost estimates at the time of scheduling 400 can: provide healthcare service consumers the information needed to budget for follow-up appointments and/or further analysis/testing healthcare service early in the process, i.e., at the time the follow-up appointments and/or further analysis/testing is being scheduled/recommended; healthcare service providers are provided the information necessary, and mechanism, to collect advance payments for follow-up appointments and/or further analysis/testing at the time the follow-up appointments and/or further analysis/testing are being recommended and/or appointments are being made; and healthcare service providers are provided the information necessary, and mechanism, to efficiently and accurately allocate time for follow-up appointments and/or further analysis/testing based on the patient's actual needs. Consequently, process for providing healthcare service appointment time and cost estimates at the time of scheduling 400 is useful in a wide range of circumstances and is not limited to the embodiments discussed in detail above.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Using process for providing healthcare service appointment time and cost estimates at the time of scheduling 400, both healthcare service consumers and healthcare service providers are provided a reliable and efficient mechanism for estimating healthcare service costs and the time to be allocated to healthcare service appointments, at the time the healthcare service appointments are being scheduled. In particular, using process for providing healthcare service appointment time and cost estimates at the time of scheduling 400, healthcare service consumers are provided the information needed to budget for healthcare service appointments early in the process, i.e., at the time the healthcare service appointment is being made; healthcare service providers are provided the information necessary, and mechanism, to collect advance payments for healthcare services at the time the healthcare service appointment is being made; and healthcare service providers are provided the information necessary, and mechanism, to efficiently and accurately allocate time for a given patient's given healthcare service appointment based on the patient's actual needs. Consequently, process for providing healthcare service appointment time and cost estimates at the time of scheduling 400 benefits both healthcare service consumers and healthcare service providers.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "accessing", "analyzing", "generating", "storing", "determining", "displaying", "transmitting", "providing", "processing", "using", "submitting", "selecting" etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s for method and apparatus and/or process or application for providing scroll bar enabled bookmarks in electronic document displays, discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A system for providing healthcare service appointment time and cost estimates at the time of scheduling comprising:
   one or more processors; and
   one or more memories coupled to the one or more processors, the one or memories having stored therein processor executable instructions which when executed by any set of the one or more processors, perform a process comprising:
   obtaining data indicating one or more healthcare services provided by a given healthcare service provider;
   obtaining code data indicating standardized codes associated with the one or more healthcare services provided by the given healthcare service provider, the data including a first set of industry standard codes and a second set of healthcare service provider-specific codes;
   determining, from the records of a healthcare insurance provider associated with the healthcare service provider, respective average appointment times for each of the one or more healthcare services provided by the given healthcare service provider;

for each of the one or more healthcare services provided by the given healthcare service provider, associating the code data with the healthcare service, and data indicating an average appointment time for the healthcare service with the healthcare service;

storing the data associated with the healthcare service in a healthcare services database;

generating data representing one or more screening questions to be asked a party at the time the party is scheduling a healthcare service appointment, the response to the one or more screening questions indicating which, if any, of the one or more healthcare services provided by the given healthcare service provider the party requires at the healthcare service appointment;

storing the data representing one or more screening questions in a screening questions database;

asking the given party the one or more screening questions, the one or more screening questions including one or more screening questions regarding the party's current symptoms;

receiving a response from the given party to the one or more screening questions;

identifying, using the response from the given party to the one or more screening questions, one or more needed services, the one or more needed services including one or more of the one or more healthcare services provided by the given healthcare service provider the party requires at the given healthcare services appointment;

determining, using the data indicating the average appointment time for the required healthcare service, an amount of time to be allotted to the given appointment; and making a healthcare service appointment for the party, the appointment being of the amount of time to be allotted, and including data indicating one or more services determined from the one or more screening questions.

2. The computing system implemented process for providing healthcare service appointment time and cost estimates at the time of scheduling of claim 1, wherein obtaining data indicating any standardized codes associated with the one or more healthcare services provided by the given healthcare service provider includes obtaining the American Medical Association CPT codes associated with the one or more healthcare services provided by the given healthcare service provider.

3. The computing system implemented process for providing healthcare service appointment time and cost estimates at the time of scheduling of claim 1, wherein obtaining data indicating any standardized codes associated with the one or more healthcare services provided by the given healthcare service provider includes obtaining the American Medical Association ICD9 codes associated with the one or more healthcare services provided by the given healthcare service provider.

4. The computing system implemented process for providing healthcare service appointment time and cost estimates at the time of scheduling of claim 1, wherein the data indicating average appointment times for the one or more healthcare services provided by the given healthcare service provider is obtained using the standardized codes associated with the one or more healthcare services provided by the given healthcare service provider.

5. The computing system implemented process for providing healthcare service appointment time and cost estimates at the time of scheduling of claim 1, wherein the one or more screening questions request at least one type of healthcare service information selected from at least one of the group of healthcare service information types consisting of:

information regarding the party's medical history and known medical conditions;

information regarding the party's previous appointments with the healthcare service provider;

information regarding whether the party has scheduled the same type of healthcare service appointment before; and information regarding the party's healthcare insurance coverage.

6. A system for providing healthcare service appointment time and cost estimates at the time of scheduling comprising:

one or more processors; and one or more memories coupled to the one or more processors, the one or memories having stored therein processor executable instructions which when executed by any set of the one or more processors, perform a process comprising:

obtaining data indicating one or more healthcare services provided by a given healthcare service provider;

obtaining code data indicating standardized codes associated with the one or more healthcare services provided by the given healthcare service provider, the data including a first set of industry standard codes and a second set of healthcare service provider-specific codes;

determining, from the records of a healthcare insurance provider associated with the healthcare service provider, respective average appointment times for each of the one or more healthcare services provided by the given healthcare service provider;

obtaining data indicating average costs associated with the one or more healthcare services provided by the given healthcare service provider;

for each of the one or more healthcare services provided by the given healthcare service provider associating the code data with the healthcare service, data indicating an average appointment time for the healthcare service, and the data indicating the average cost of the healthcare service with the healthcare service;

storing the data associated with the healthcare service in a healthcare services database;

generating data representing one or more screening questions to be asked a party at the time the party is scheduling a healthcare service appointment, the response to the one or more screening questions indicating which, if any, of the one or more healthcare services provided by the given healthcare service provider the party requires at the healthcare service appointment;

storing the data representing one or more screening questions in a screening questions database;

asking the given party the one or more screening questions, the one or more screening questions including one or more screening questions regarding the party's current symptoms;

receiving a response from the given party to the one or more screening questions;

identifying, using the response from the given party to the one or more screening questions, one or more needed services, the one or more needed services including one or more of the one or more healthcare services provided by the given healthcare service provider the party requires at the given healthcare services appointment;

determining, using the data indicating the average appointment time for the required healthcare service, an amount of time to be allotted to the given appointment;

making a healthcare service appointment for the party, the appointment being of the amount of time to be allotted, and including data indicating one or more services determined from the one or more screening questions; and using, at least in part, the data indicating the average cost for the required healthcare service in the healthcare services database to estimate the given party's out-of-pocket cost for the given appointment when the given appointment is being made using the computing system implemented healthcare services appointment system.

7. A computer program product for providing healthcare service appointment time and cost estimates at the time of scheduling comprising:

a nontransitory computer readable medium, the computer readable medium having stored thereon instructions when executed by any set of one or more processors perform a process comprising:

obtaining data indicating one or more healthcare services provided by a given healthcare service provider;

obtaining code data indicating standardized codes associated with the one or more healthcare services provided by the given healthcare service provider, the data including a first set of industry standard codes and a second set of healthcare service provider-specific codes;

determining, from the records of a healthcare insurance provider associated with the healthcare service provider, respective average appointment times for each of the one or more healthcare services provided by the given healthcare service provider;

for each of the one or more healthcare services provided by the given healthcare service provider associating the code data with the healthcare service, and data indicating an average appointment time for the healthcare service with the healthcare service;

storing the data associated with the healthcare service in a healthcare services database;

generating data representing one or more screening questions to be asked a party at the time the party is scheduling a healthcare service appointment, the response to the one or more screening questions indicating which, if any, of the one or more healthcare services provided by the given healthcare service provider the party requires at the healthcare service appointment;

storing the data representing one or more screening questions in a screening questions database;

asking the given party the one or more screening questions, the one or more screening questions including one or more screening questions regarding the party's current symptoms;

receiving a response from the given party to the one or more screening questions;

identifying, using the response from the given party to the one or more screening questions, one or more needed services, the one or more needed services including one or more of the one or more healthcare services provided by the given healthcare service provider the party requires at the given healthcare services appointment;

determining, using data indicating the average appointment time for the required healthcare service, an amount of time to be allotted to the given appointment; and making a healthcare service appointment for the party, the appointment being of the amount of time to be allotted, and including data indicating one or more services determined from the one or more screening questions.

8. The computer program product for providing healthcare service appointment time and cost estimates at the time of scheduling of claim 7, wherein obtaining data indicating any standardized codes associated with the one or more healthcare services provided by the given healthcare service provider includes obtaining the American Medical Association CPT codes associated with the one or more healthcare services provided by the given healthcare service provider.

9. The computer program product for providing healthcare service appointment time and cost estimates at the time of scheduling of claim 7, wherein obtaining data indicating any standardized codes associated with the one or more healthcare services provided by the given healthcare service provider includes obtaining the American Medical Association ICD9 codes associated with the one or more healthcare services provided by the given healthcare service provider.

10. The computer program product for providing healthcare service appointment time and cost estimates at the time of scheduling of claim 7, wherein the data indicating average appointment times for the one or more healthcare services provided by the given healthcare service provider is obtained using the standardized codes associated with the one or more healthcare services provided by the given healthcare service provider.

11. The computer program product for providing healthcare service appointment time and cost estimates at the time of scheduling of claim 7, wherein the one or more screening questions request at least one type of healthcare service information selected from at least one of the group of healthcare service information types consisting of:

information regarding the party's medical history and known medical conditions;

information regarding the party's previous appointments with the healthcare service provider;

information regarding whether the party has scheduled the same type of healthcare service appointment before; and information regarding the party's healthcare insurance coverage.

12. A computer program product for providing healthcare service appointment time and cost estimates at the time of scheduling comprising:

a nontransitory computer readable medium, the computer readable medium having stored thereon instructions when executed by any set of one or more processors perform a process comprising:

obtaining data indicating one or more healthcare services provided by a given healthcare service provider;

obtaining code data indicating standardized codes associated with the one or more healthcare services provided by the given healthcare service provider, the data including a first set of industry standard codes and a second set of healthcare service provider-specific codes;

determining, from the records of a healthcare insurance provider associated with the healthcare service provider, respective average appointment times for each of the one or more healthcare services provided by the given healthcare service provider;

obtaining data indicating average costs associated with the one or more healthcare services provided by the given healthcare service provider;

for each of the one or more healthcare services provided by the given healthcare service provider associating the code data with the healthcare service, data indicating an average appointment time for the healthcare service, and the data indicating the average cost of the healthcare service with the healthcare service;

storing the data associated with the healthcare service in a healthcare services database;

generating data representing one or more screening questions to be asked a party at the time the party is scheduling a healthcare service appointment, the response to the one or more screening questions indicating which, if any, of the one or more healthcare services provided by the given healthcare service provider the party requires at the healthcare service appointment;

storing the data representing one or more screening questions in a screening questions database;

asking the given party the one or more screening questions, the one or more screening questions including one or more screening questions regarding the party's current symptoms;

receiving a response from the given party to the one or more screening questions;

identifying, using the response from the given party to the one or more screening questions, one or more needed services, the one or more needed services including one or more of the one or more healthcare services provided by the given healthcare service provider the party requires at the given healthcare services appointment;

determining, using the data indicating the average appointment time for the required healthcare service, an amount of time to be allotted to the given appointment;

making a healthcare service appointment for the party, the appointment being of the amount of time to be allotted, and including data indicating one or more services determined from the one or more screening questions; and using, at least in part, the data indicating the average cost for the required healthcare service in the healthcare services database to estimate the given party's out-of-pocket cost for the given appointment when the given appointment is being made using the computing system implemented healthcare services appointment system.

\* \* \* \* \*